United States Patent [19]

Rivier et al.

[11] Patent Number: 5,278,146
[45] Date of Patent: Jan. 11, 1994

[54] CRF ANALOGS

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 905,564

[22] Filed: Jun. 29, 1992

Related U.S. Application Data

[63] Continuation-in-part of Ser. No. 498,230, Mar. 23, 1990, abandoned, which is a continuation-in-part of Ser. No. 251,674, Sep. 30, 1988, abandoned.

[51] Int. Cl.$^5$ .................... A61K 37/40; C07K 7/38
[52] U.S. Cl. ................................ 514/12; 514/2; 530/306; 530/324; 530/325; 930/70; 930/DIG. 800; 930/DIG. 820; 930/DIG. 822
[58] Field of Search .............. 530/306, 324, 325; 514/12, 2; 930/70, DIG. 800, 820, 822

[56] References Cited

U.S. PATENT DOCUMENTS

| | | | |
|---|---|---|---|
| 4,489,163 | 12/1984 | Rivier et al. | 436/86 |
| 4,594,329 | 6/1986 | Vale, Jr. et al. | 514/12 |
| 5,112,809 | 5/1992 | Rivier et al. | 514/12 |

*Primary Examiner*—Lester L. Lee
*Assistant Examiner*—T. D. Wessendorf
*Attorney, Agent, or Firm*—Fitch, Even, Tabin & Flannery

[57] ABSTRACT

Analogs of CRF, which are based upon hCRF, oCRF, sauvagine and alpha-helical CRF, are disclosed that can be administered to achieve a substantial elevation of ACTH, β-endorphin, β-lipotropin, other products of the pro-opiomelanocortin gene and corticosterone levels and/or an increase in blood pressure over an extended period of time. One CRF agonist which has been found to be particularly potent is: H-Ser-Gln-Glu-Pro-Pro-Ile-Ser-Leu-Asp-Leu-Thr-D-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala-NH$_2$. In these agonist analogs, one or more of the first six N-terminal residues may be deleted and/or the N-terminal alpha-amino group may be acylated by an acylating agent containing up to 7 carbon atoms. A number of other substitutions may also be made throughout the chain. These analogs or pharmaceutically or veterinarily acceptable salts thereof, dispersed in a pharmaceutically or veterinarily acceptable liquid or solid carrier, can be administered to mammals, including humans. These analogs may also be used as stimulants to elevate mood and improve memory and learning, as well as diagnostically.

11 Claims, No Drawings

CRF ANALOGS

This invention was made with Government support under Grant Nos. HD-13527 and DK-26741, awarded by the National Institutes of Health. The Government has certain rights in this invention.

This application is a continuation-in-part of our application Ser. No. 498,230, filed Mar. 23, 1990, which was a continuation-in-part of our earlier application Ser. No. 251,674, filed Sep. 30, 1988, both now abandoned.

This invention is directed to peptides and to methods for pharmaceutical treatment of mammals using such peptides. More specifically, the invention relates to analogs of the hentetracontapeptide CRF, to pharmaceutical compositions containing such CRF analogs and to methods of treatment of mammals using such CRF analogs.

BACKGROUND OF THE INVENTION

Experimental and clinical observations have supported the concept that the hypothalamus plays a key role in the regulation of adenohypophysial corticotropic cells secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. None of the secretagogs characterized met the criteria expected of a physiologic corticotropin releasing factor (CRF) until ovine CRF (oCRF) was characterized in 1981 as disclosed in U.S. Pat. No. 4,415,558, the disclosure of which is incorporated herein by reference. oCRF lowers blood pressure in mammals and stimulates the secretion of ACTH and $\beta$-endorphin.

Rat CRF(rCRF) has been isolated, purified and characterized as a homologous hentetracontapeptide as disclosed in U.S. Pat. No. 4,489,163, the disclosure of which is incorporated herein by reference. The formula of human CRF has now been determined to be the same as that of rCRF, and the terms rCRF and hCRF are used interchangeably. Synthetic rCRF and oCRF stimulate ACTH and $\beta$-endorphin-like activities ($\beta$-END-LI) in vitro and in vivo and substantially lower blood pressure when injected peripherally, e.g. intravenously.

SUMMARY OF THE INVENTION

Analogs of these 41-residue CRF peptides have been discovered which exhibit at least about the same biological activity D vitro as the native peptides (thus being conventionally referred to as CRF agonists) and which have substantially longer duration of biological effect vivo. These CRF agonist peptides have at least one and preferably at least 2 of the following D-isomer substitutions: D-Phe in the 12-position, D-Glu in the 20-position, D-Ala in the 24-position and D-His in the 32-position. Norleucine may be substituted in the 18, 21 and/or 38 positions. The residues in the 8, 12, 19, 21, 22, 24, 27, 28, 32, 33, 36, 38, 40 and/or 41 positions, and particularly the residue in the 37 position can be substituted with a methyl group on its o-carbon atom. The N-terminus can be optionally shortened by from one to a sequence of up to 6 residues, and the N-terminal residue may be acylated.

Pharmaceutical compositions in accordance with the invention include such CRF agonists, or nontoxic addition salts thereof, dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, $\beta$-endorphin, $\beta$-lipotropin, other products of the pro-opiomelano-cortin gene and corti-costerone and/or for the lowering of blood pressure and/or for affecting mood, behavioral and gastrointestinal functions and autonomic nervous system activities. Furthermore such CRF agonists may be used for the evaluation of the status of pituitary, cardiovascular, gastrointestinal or central nervous system functions.

DETAILED DESCRIPTION OF THE PRFRRED EMBODIMETS

The nomenclature used to define the peptides is that specified by Schroder & Lubke, "The Peptides", Academic press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline and Har=L-homoarginine. In addition the following 2 representations are used: leu=either L-leucine or $C^\alpha CH_3$-L-leucine(CML); ala=either L-alanine or $C^\alpha CH_3$-L-alanine(CMA).

The invention provides agonists of CRF having at least one D-isomer and the following Formula (I): Y-$R_1$-$R_2$-$R_3$-$R_4$-$R_5$-$R_6$-Ser-Leu-Asp-Leu-Thr-$R_{12}$-His-Leu-Leu-Arg-Glu-Val-Leu-$R_{20}$-$R_{21}$-$R_{22}$-$R_{23}$-$R_{24}$-$R_{25}$-Gln-Leu-Ala-Gln-Gln-Ala-$R_{32}$-Ser-Asn-Arg-Lys-$R_{37}$-$R_{38}$-$R_{39}$-Ile-$R_{41}$-$NH_2$, wherein Y is an acyl group having 7 or fewer carbon atoms or hydrogen; $R_1$ is Ser or des$R_1$; $R_2$ is Glu, Gln, pGlu or des$R_2$; $R_3$ is Glu or des$R_3$; $R_4$ is Pro or des$R_4$; $R_5$ is Pro or des$R_5$; $R_6$ is Ile or des$R_6$; $R_{12}$ is D-Phe or Phe; $R_{20}$ is D-Glu or Glu; $R_{21}$ is Met or Nle; $R_{22}$ is Ala or Thr; $R_{23}$ is Arg or Lys; R$R_{24}$ is D-Ala or Ala; $R_{25}$ is Glu or Asp; $R_{32}$ is D-His or His; $R_{37}$ is leu; $R_{38}$ is Met, Nle or Leu; $R_{39}$ is Glu or Asp; $R_{41}$ is Ile or Ala; provided however that at least one of the following residues is present: $R_{12}$ is D-Phe, Re is D-Glu, $R_{24}$ is D-Ala, and $R_{32}$ is D-His. Nontoxic addition salts of these peptides can be used as well. Preferably both D-Phe in the 12-position and D-Glu in the 20-position are present, or at least one is present. These analogs remain potent even if slightly shortened at the N-terminus, i.e., by a sequence of up to about 6 residues.

In a broader sense, the invention provides analogs of CRF containing at least one D-isomer and having the following Formula (II): Y-$R_1$-$R_2$-$R_3$-$R_4$-$R_5$-$R_6$-Ser-$R_{11}$-$R_{12}$-$R_{13}$-$R_{14}$-Leu-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-Gln-Ala-$R_{32}$-$R_{33}$-Asn-Arg-$R_{36}$-$R_{37}$-$R_{38}$-$R_{39}$-$R_{40}$-$R_{41}$-$NH_2$ wherein Y is an acyl group having 7 or fewer carbon atoms or hydrogen; $R_1$ is Ser, D-Ser or des$R_1$; $R_2$ is Glu, Gln, pGlu, D-pGlu or des$R_2$; $R_3$ is Glu, Gly, D-Tyr or des$R_3$; $R_4$ is Pro, D-Pro or des$R_4$; $R_5$ is Pro or des$R_5$; $R_6$ is Ile or des$R_6$; $R_8$ and $R_{19}$ are selected from the group consisting of leu, Ile, ala, Gly, Val, Nle, Phe and Gln; $R_9$ is Asp or Glu; $R_{11}$ is Thr or Ser; $R_{12}$ is Phe, D-Phe, leu, ala, Ile, Gly, Val, Nle or Gln; $R_{13}$ is His, Tyr or Glu; $R_{14}$ is Leu or Met; $R_{17}$; is Glu or Lys; $R_{18}$ is Val, Nle or Met; $R_{20}$ is His, D-Glu or Glu; $R_{21}$ is Arg, Met, Nva, Ile, ala, leu, Nle, Val, Phe or Gln; $R_{22}$ is ala, Thr, Asp or Glu; $R_{23}$ is Arg, Orn, Har or Lys; $R_{24}$ is ala, D-Ala, Met, leu, Ile, Gly, Val, Nle, Phe and Gln; $R_{25}$ is Glu or Asp; $R_{26}$ is Gly, Gln, Asn or Lys; $R_{27}$ is leu, Ile, ala, Val, Nva, Met, Nle, Phe, Asp, Asn, Gln or Glu; $R_{28}$ is ala, Arg or Lys; $R_{29}$ is Gln or Glu; $R_{32}$ is leu, His, D-His, Gly, Tyr or ala; $R_{33}$ is Ile, Ser, Asn, leu, Thr or ala; $R_{36}$ is Asn, Lys, Orn, Arg, Har or leu; $R_{37}$ is leu or Tyr; $R_{38}$ is Met, Nle or leu; $R_{39}$ is Glu or Asp; $R_{40}$ is Ile, Thr, Glu, ala, Val, leu, Nle, Phe, Nva, Gly, Asn or Gln; $R_{41}$ is Ile, ala, Gly, Val, leu, Nle, Phe or Gln, provided however that at least one of the following residues is present: $R_{12}$ is D-Phe, $R_{20}$ is D-Glu, $R_{24}$ is D-Ala, $R_{32}$ is D-His and $R_{37}$ is CML, as well as nontoxic salts thereof.

A preferred subgroup of these CRF agonist peptides includes those analogs of either oCRF or rCRF wherein D-Phe is present in the 12-position, the residues present in the 21 and 38-positions can optionally be substituted by Nle, and the residue present in the 36-position can be substituted by Leu. Particularly preferred are CRF agonists having the following formula: H-Ser-Glu-Glu-Pro-Pro-Ile-Ser-Leu-Asp-Leu-Thr-D-Phe-His-Leu-Leu-Arg-Glu-Val-Leu-Glu-$R_{21}$-Ala-Arg-Ala-Glu-Gln-Leu-Ala-Gln-Gln-Ala-His-Ser-Asn-Arg-$R_{36}$-Leu-$R_{38}$-Glu-Ile-Ile-NH$_2$, and H-Ser-Gln-Glu-Pro-Pro-Ile-Ser-Leu-Asp-Leu-Thr-D-Phe-His-Leu-Leu-Arg-Glu-Val-Leu-Glu-$R_{21}$-Thr-Lys-Ala-Asp-Gln-Leu-Ala-Gln-Gln-Ala-His-Ser-Asn-Arg-$R_{36}$-Leu-$R_{38}$-Asp-Ile-Ala-NH$_2$, wherein $R_{38}$ is Met or Nle; $R_{36}$ is Leu or Lys; and $R_{38}$ is Met, Leu or Nle; provided however that the N-terminus may be shortened by one or a sequence of up to six residues.

A CRF peptide having a high alpha-helical forming potential is disclosed in U.S. Pat. No. 4,594,329, the disclosure of which is incorporated herein by reference, and is referred to as AHC. Another subgroup of CRF agonists which are at least as potent as native CRF are those based upon AHC having the following formula, including at least one D-isomer: Y-$R_1$-$R_2$-$R_3$-$R_4$-$r_5$-$R_6$-Ser-Leu-$R_9$-Leu-Thr-$R_{12}$-$R_{13}$-$R_{14}$-Leu-Arg-Glu-$R_{18}$-Leu-$R_{20}$-$R_{21}$-Ala-Lys-$R_{24}$-Glu-Gln-$R_{27}$-Ala-Glu-Gln-Ala-$R_{32}$-$R_{33}$-Asn-Arg-$R_{36}$-$R_{37}$-$R_{38}$-$R_{39}$-$R_{40}$-$R_{41}$-NH$_2$ wherein Y is an acyl group having 7 or fewer carbon atoms or hydrogen; $R_1$ is Ser or desR$_1$; $R_2$ is Glu, Gln or desR$_2$; $R_3$ is Glu or desR$_3$; $R_4$ is Pro or desR$_4$; $R_5$ is Pro or desR$_5$; $R_6$ is Ile or desR$_6$; $R_9$ is Asp or Glu; $R_{12}$ is Phe, D-Phe or Leu; $R_{13}$ is His or Glu; $R_{14}$ is Leu or Met; $R_{16}$ is Nle or Met; $R_{20}$ is His, D-Glu or Glu; $R_{21}$ is Met, Nle or Ile; $R_{24}$ is Ala or D-Ala; $R_{27}$ is Glu or Leu; $R_{32}$ is His, D-His or Ala; $R_{33}$ is Ser or Leu; $R_{36}$ is Leu or Lys; $R_{37}$ is leu or Tyr; $R_{38}$ is Leu or Nle; $R_{39}$ is Glu or Asp; $R_{40}$ is Ile or Glu and $R_{41}$ is Ile, Ala or Val; provided however that at least one of the following residues is present: $R_{12}$ is D-Phe, $R_{20}$ is D-Glu, $R_{24}$ is D-Ala, and $R_{32}$ is D-His. Analogs of AHC containing at least one of the four above-specified D-isomers exhibit biological potency and remain potent even if slightly shortened at the N-terminus, i.e., by a sequence of up to about 6 residues.

The peptides are synthesized by a suitable method, such as by exclusively solid-phase techniques, by partial solid-phase techniques, by fragment condensation or by classical solution addition. Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Thus, chemical synthesis of one example of such a CRF agonist may result in the formation of an intermediate of the Formula (IA): $X^1$-$R_1(X^2)$-$R_2(X^4$ or $X^5)$-$R_3(X^5)$-$R_4$-$R_5$-Ile-Ser($X^2$)-Leu-Asp($X^5$)-Leu-Thr($X^2$)-D-Phe-His($X^7$)-Leu-Leu-Arg($X^3$)-Glu($X^5$)-Val-Leu-$R_{20}(X^5)$-$R_{21}R_{22}(X^2)$-$R_{23}(X^3$or $X^6)$-$R_{24}$-$R_{25}(X^5)$-Gln($X^4$)-Leu-Ala-Gln($X^4$)-Gln($X^4$)-Ala-$R_{32}(X^7)$-Ser($X^2$)-Asn($X^4$)-Arg($X^3$)-Lys($X^6$)-leu-$R_{38}$-$R_{39}(X^5)$-Ile-$R_{41}$-$X^8$ wherein: the R-groups are as hereinbefore defined.

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxy-carbonyl; (4) cycloalkyl urethan-type protecting groups, such as fluorenylmethyloxycarbonyl(FMOC), cyclopentyloxycarbonyl, adamantyloxycarbonyl, and cyclohexyloxycarbonyl; and (5) thiourethan-type protecting groups, such as phenylthiocarbonyl. The preferred alpha-amino protecting group is BOC if the synthesis employs acid-catalyzed removal of the alpha-amino protecting groups; however, for syntheses employing a base-catalyzed removal strategy, FMOC is preferred, in which case more acid-labile side-chain protecting groups can be used, including t-Butyl esters or ethers as well as BOC.

$X^2$ is a protecting group for the hydroxyl group of Thr and Ser and is generally selected from the class containing acetyl(Ac), benzoyl(Bz), tert-butyl(t-Bu), triphenylmethyl(trityl), tetrahydropyranyl, benzyl ether(Bzl) and 2,6-dichlorobenzyl(DCB) when a BOC strategy is employed. The preferred protecting group is Bzl for a BOC strategy and t-Bu for FMOC strategy. $X^2$ can also be hydrogen, which means there is no protecting group on the hydroxyl group.

$X^3$ is a protecting group for the guanidino group of Arg generally selected from the class containing nitro, p-toluenesulfonyl(Tos), Z, adamantyloxycarbonyl and BOC, or is hydrogen. Tos is preferred for a BOC strategy and 4-methoxy-2,3,6-trimethyl benzene sulfonyl (MTR) or pentamethylchroman-6-sulfonyl(PMC) for FMOC strategy.

$X^4$ is hydrogen or a protecting group, preferably xanthyl(Xan), for the amido group of Asn or Gln.

$X^5$ is hydrogen or an ester-forming protecting group for the β- or γ-carboxyl group of Asp or Glu, and is generally selected from the class containing the esters of cyclohexyl(OChx), benzyl(OBzl), 2,6-dichlorobenzyl, methyl, ethyl and t-butyl(Ot-Bu). OChx is preferred for a BOC strategy and Ot-Bu for FMOC strategy.

$X^6$ is hydrogen or a protecting group for the side chain amino substituent of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore. 2-Cl-Z is preferred for a BOC strategy and BOC for FMOC strategy.

$X^7$ is hydrogen or a protecting group for the imidazole nitrogen of His such as Tos or 2,4-dinitrophenyl(DNP).

When Met is present, the sulfur may be protected, if desired, with oxygen.

The selection of a side chain amino protecting group is not critical except that it must be one which is not removed during deprotection of the alpha-amino groups during the synthesis. Hence, the alpha-amino protecting group and the side chain amino protecting group cannot be the same.

$X^8$ is $NH_2$, a protecting group such as an ester or an anchoring bond used in solid phase synthesis for linking to a solid resin support, preferably one represented by the formulae:

—NH-benzhydrylamine (BHA) resin support and —NH-paramethylbenzhydrylamine (MBHA) resin support. Cleavage from a BHA or MBHA resin directly gives the CRF analog amide. By employing an N-methyl-derivative of such a resin, a methyl-substituted amide can be created.

In the formula for the intermediate, at least one of $X^1$, $X^2$, $X^3$, $X^4$, $X^5$, $X^6$ and $X^7$ is a protecting group. The particular amino acid chosen for each the R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selecte for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the acyl group at the N-terminal represented by Y, acetyl, formyl, acrylyl and benzoyl are preferred. Moreover, as indicated hereinbefore, the N-terminus can be slightly shortened without significantl affecting biological potency.

Thus, there is also disclosed herein processes for the manufacture of compounds defined by the Formula (I) comprising (a) forming a peptide intermediate having at least one protective group and having the Formula (IA) wherein: $X^1$, $X^2$, $X^3$, $X^4$, $X^5$, $X^6$ and $X^7$ are each either hydrogen or a protective group, and $X^8$ is either a protective group or an anchoring bond to resin support or $NH_2$ and (b) splitting off the protective group or groups or anchoring bond from said peptide intermediate of the Formula (II) and (c) if desired, converting a resulting peptide into a nontoxic addition salt thereof.

When the peptides are prepared by chemical synthesis, they are preferably prepared using solid phase synthesis, such as that described by Merrifield, *J Am. Chem. Soc.*, 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for rCRF analogs can be prepared by attaching alpha-amino-protected Ile to a BHA resin.

Ile protected by BOC is coupled to the BHA resin using methylene chloride and dimethylformamide (DMF). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0-5 weight % 1,2 ethanedithiol. The deprotection is carried out at a temperature between about 0° C. and room temperature. Other standard cleaving reagents and conditions for removal of specific alpha-amino protecting groups may be used as described in Schroder & Lubke, "The Peptides", 1 pp 72–75 (Academic Press 1965).

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCC) and N,N'-diisopropyl carbodiimide(DICI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl) carbodiimide. Other activating reagents and their use in peptide coupling are described by Schroder & Lubke, supra, in Chapter III, and by Kapoor, *J. Phar. Sci.*, 59, pp 127 (1970).

Each protected amino acid or amino acid sequence is introduced into the solid phase reactor in about a fourfold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp.1927–1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$ and $X^7$ and the alpha-amino protecting group $X^1$ (unless it is an acyl group which is intended to be present in the final peptide) to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate potential S-alkylation.

The following Example sets forth the preferred method for synthesizing CRF analogs by the solid-phase technique.

EXAMPLE I

The synthesis of [D-Glu$^{20}$]-rCRF having the formula: H-Ser-Glu-Glu-Pro-Pro-Ile-Ser-Leu-Asp-Leu-Thr-Phe-His-Leu-Leu-Arg-Glu-Val-Leu-D-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$ is conducted in a stepwise manner on a MBHA hydrochloride resin, such as available from Bachem, Inc., having a substitution range of about 0.1 to 0.5 mmoles/gm. resin. The synthesis is performed on an automatic Beckman 990B peptide synthesizer using a suitable program, preferably as follows:

| STEP MIN. | REAGENTS AND OPERATIONS | MIX TIMES |
|---|---|---|
| 1 | CH$_2$Cl$_2$ wash-80 ml. (2 times) | 3 |
| 2 | Methanol(MeOH) wash-30 ml. (2 times) | 3 |
| 3 | CH$_2$Cl$_2$ wash-80 ml. (3 times) | 3 |
| 4 | 50 percent TFA plus 5 percent 1,2-ethanedithiol in CH$_2$Cl$_2$-70 ml. (2 times) | 12 |
| 5 | Isopropanol wash-80 ml. (2 times) | 3 |
| 6 | TEA 12.5 percent in CH$_2$Cl$_2$-70 ml. (2 times) | 5 |
| 7 | MeOH wash-40 ml. (2 times) | 2 |
| 8 | CH$_2$Cl$_2$ wash-80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30-300 |

Coupling of BOC-Ile results in the substitution of about 0.35 mmol. Ile per gram of resin. All solvents that are used are carefully degassed, preferably by sparging with an inert gas, e.g., helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) can be used to activate the carboxyl end of Asn or Gln; for example, BOC-Asn(ONp) can be coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain. Tos is used to protect the guanidino group of Arg and the imidazole group of His, and the side-chain carboxyl group of Glu or Asp is protected by OBzl. At the end of the synthesis, the following composition is obtained: BOC-Ser(Bzl)-Glu(OBzl)-Glu(OBzl)-Pro-Pro-Ile-Ser(Bzl)-Leu-Asp(OBzl)-Leu-Thr(Bzl)-Phe-His(Tos)-Leu-Leu-Arg(Tos)-Glu(OBzl)-Val-Leu-D-Glu(OBzl)-Met-Ala-Arg(Tos)-Ala-Glu(OBzl)-Gln(Xan)-Leu-Ala-Gln(Xan)-Gln(Xan)-Ala-His(Tos)-Ser(Bzl)-Asn(Xan)-Arg(Tos)-Lys(2-Cl-Z)-Leu-Met-Glu(OBzl)-Ile-Ile-resin support. Xan may have been partially or totally removed by TFA treatment used to deblock the alpha-amino protecting group.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0° C. for one-half hour. After elimination of the HF under high vacuum, the resin-peptide is washed alternately with dry diethyl ether and chloroform, and the peptides are then extracted with degassed 2N aqueous acetic acid and separated from the resin by filtration.

The peptide is purified by gel permeation followed by preparative HPLC as described in Marki, et al., *J. Am. Chem. Soc.*, 103, 3178 (1981); Rivier, et al., *J. Chromatography*, 288, 303-328 (1984); and Hoeger, et al., *BioChromatography*, 2, 3, 134-142 (1987). The chromatographic fractions are carefully monitored by HPLC, and only the fractions showing substantial purity are pooled.

To check whether the precise sequence is achieved, the rCRF analog is hydrolyzed in sealed evacuated tubes containing constant boiling HCl, 3 μl of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 41-residue peptide structure has been obtained.

EXAMPLE II

The peptide [D-Glu$^{20}$]-oCRF having the formula: H-Ser-Gln-Glu-Pro-Pro-Ile-Ser-Leu-Asp-Leu-Thr-Phe-His-Leu-Leu-Arg-Glu-Val-Leu-D-Glu-Met-Thr-Lys-Ala-Asp-Gln-Leu-Ala-Gln-Gln-Ala-His-Ser-Asn-Arg-Lys-Leu-Leu-Asp-Ile-Ala-NH$_2$ is synthesized using a procedure generally as set forth in Example I.

Specific optical rotation of the hCRF peptide, which is synthesized and purified in the foregoing manner, is measured on a Perkin Elmer Model 241 Polarimeter as $[\alpha]_D^{22} = -77.6 \pm 1.0$ (c=0.5 in 1% acetic acid) (with correction for the presence of H$_2$O and TFA); it has a purity of about 98.8%.

The peptide is judged to be homogeneous using thin layer chromatography and several different solvent systems. It is specifically subjected to reversed-phase high pressure liquid chromatography using a Waters HPLC system with a 0.46×25 cm. column packed with 5 μm C$_{18}$ silica, 300 Å pore size. Buffer A which is used is an aqueous 0.1% trifluoroacetic acid solution consisting of 1.0 ml. of TFA per 1000 ml. of solution; Buffer B is 100% acetonitrile. The determination is run at room temperature with a gradient from 15.5% Buffer B to 71.5% Buffer B over 30 minutes. The flow rate is 1.8 ml. per minute, and the retention time is 23.0 minutes.

Amino acid analysis of the resultant, purified peptide is consistent with the formula for the prepared peptide and confirms that the 41-residue peptide structure is obtained.

EXAMPLE III

The peptide [D-Glu$^{20}$ CML$^{37}$]-oCRF having the formula: H-Ser-Gln-Glu-Pro-Pro-Ile-Ser-Leu-Asp-Leu-Thr-Phe-His-Leu-T-Arg-Glu-Val-Leu-D-Glu-Met-Thr-Lys-Ala-Asp-Gln-Leu-Ala-Gln-Gln-Ala-His- Ser-Asn-Arg-Lys-CML-T-Asp-Ile-Ala-NH₂ is synthesized using a procedure generally as set forth in Example I.

The peptide is judged to be homogeneous using thin layer chromatography and several different solvent systems. It is specifically subjected to reversed-phase high pressure liquid chromatography using a Waters HPLC system with a 0.46×25 cm. column packed with 5 μm C₁₈ silica, 300 Å pore size. Amino acid analysis of the resultant, purified peptide is consistent with the formula for the prepared peptide and confirms that the 41-residue peptide structure is obtained.

The synthetic peptide [D-Glu²⁰]-oCRF is examined for its effects on the secretion of ACTH and β-endorphin vitro and was also in vivo. The potency of synthetic [D-Glu²⁰]-oCRF to stimulate the secretion of ACTH and β-endorphin by cultured rat pituitary cells is measured using the procedure as generally set forth in *Endocrinology*, 91, 562 (1972) and compared against synthetic oCRF. Half-maximal responses are observed at about 170 picomolar concentrations of the peptide [D-Glu²⁰]-oCRF, while synthetic oCRF concentrations of about 250 picomolar are needed to achieve this response. The secretory response to maximal (1-5 nM) concentrations of [D-Glu²⁰]-oCRF is at a plateau level; it is considered to be about twice as potent as the native hormone. vivo testing is carried out using the general procedure set forth in C. Rivier et al., *Science*, 218, 377 (1982) and shows longer duration of potency and a significant lowering of blood pressure when administered peripherally.

EXAMPLE IV

The peptide [D-Phe¹², D-Glu²⁰]-rCRF(3–41) having the formula: H-Glu-Pro-Pro-Ile-Ser-Leu-Asp-Leu-Thr-D-Phe-His-Leu-Leu-Arg-Glu-Val-Leu-D-Glu-Met-Ala-Arg-Ala-Glu-Gln-Leu-Ala-Gln-Gln-Ala-His-Ser-Asn-Arg-Lys-Leu-Met-Glu-Ile-Ile-NH₂ is synthesized. Amino acid analysis of the resultant, purified peptide is consistent with the formula for the prepared peptide and confirms that the 39-residue peptide structure is obtained. Testing in accordance with the general procedure set forth in Example III shows that it likewise stimulates the secretion of ACTH and β-END-LI and causes a very significant lowering of blood pressure when administered peripherally.

EXAMPLE V

The peptide [D-Glu²⁰, Nle²¹]-oCRF having the formula: H-Ser-Gln-Glu-Pro-Pro-Ile-Ser-Leu-Asp-Leu-Thr-Phe-His-Leu-Leu-Arg-Glu-Val-Leu-D-Glu-Nle-Thr-Lys-Ala-Asp-Gln-Leu-Ala-Gln-Gln-Ala-His-Ser-Asn-Arg-Lys-Leu-Leu-Asp-Ile-Ala-NH₂ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and β-END-LI and causes a very significant lowering of blood pressure when administered peripherally.

EXAMPLE VI

The peptide [Acetyl-Ser¹, D-Phe¹², Nle²¹,³⁸]-rCRF having the formula: Ac-Ser-Glu-Glu-Pro-Pro-Ile-Ser-Leu-Asp-Leu-Thr-D-Phe-His-Tu-Leu-Arg-Glu-Val-Leu-Glu-Nle-Ala-Arg-Ala-Glu-Gln-Tu-Ala-Gln-Gln-Ala-His-Ser-Asn-Arg-Lys-Leu-Nle-Glu-Ile-Ile-NH₂ is synthesized. Amino acid analysis of the resultant, purified peptide is consistent with the formula for the prepared peptide and confirms that the 41-residue peptide structure is obtained. The synthesis is repeated to produce the sa=peptide without the N-acetylation at the N-terminus. Testing in accordance with the general procedure set forth hereinbefore shows that both peptides stimulate the secretion of ACTH and β-END-LI and cause a very significant lowering of blood pressure.

EXAMPLE VII

The peptide [D-Phe¹²]-oCRF having the formula: H-Ser-Gln-Glu-Pro-Pro-Ile-Ser-Leu-Asp-Leu-Thr-D-Phe-His-Leu-Leu-Arg-Glu-Val-Leu-Glu-Met-Thr-,Lys-Ala-Asp-Gln-Leu-Ala-Gln-Gln-Ala-His-Ser-Asn-Arg-Lys-Leu-Leu-Asp-Ile-Ala-NH₂ is synthesized using a procedure generally as set forth in Example I.

Specific optical rotation of the oCRF analog peptide, which is synthesized and purified in the foregoing manner, is measured on a Perkin Elmer Model 241 Polarimeter as $[\alpha]_D^{22} = -75.3 \pm 1.0$ (c=0.5 in 1% acetic acid) (with correction for the presence of H₂O and TFA); it has a purity of greater than 98%.

The peptide is judged to be homogeneous using thin layer chromatography and several different solvent systems. It is specifically subjected to reversed-phase high pressure liquid chromatography using the Waters HPLC system with a 0.46×25 cm. column packed with 5 μm C₁₈ silica, 300 Å pore size. Buffer A which is used is an aqueous 0.1% trifluoroacetic acid solution consisting of 1.0 ml. of TFA per 1000 ml. of solution; Buffer B is 100% acetonitrile. The determination is run at room temperature with a gradient from 9% Buffer B to 57.0% Buffer B over 30 minutes. The flow rate is 1.8 ml. per minute, and the retention time is 28.3 minutes.

Amino acid analysis of the resultant, purified peptide is consistent with the formula for the prepared peptide and confirms that the 41-residue peptide structure is obtained.

EXAMPLE VIII

The peptide [D-Phe¹², D-Ala²⁴]-rCRF(4–41) having the formula: H-Pro-Pro-Ile-Ser-Leu-Asp-Leu-Thr-D-Phe-His-Leu-Leu-Arg-Glu-Val-Leu-Glu-Met-Ala-Arg-D-Ala-Glu-Gln-Tu-Ala-Gln-Gln-Ala-His-Ser-Asn-Arg-Lys-Leu-Met-Glu-Ile-Ile-NH₂ is synthesized. Amino acid analysis of the resultant, purified peptide is consistent with the formula for the prepared peptide and confirms that the 38-residue peptide structure is obtained. Testing in accordance with the general procedure set forth hereinbefore shows that it likewise stimulates the secretion of ACTH and β-END-LI and causes a very significant lowering of blood pressure.

EXAMPLE IX

The peptide [D-Phe¹², Nle²¹]-oCRF having the formula: H-Ser-Gln-Glu-Pro-Pro-Ile-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Gln-Ala-His-Ser-Asn-Arg-Lys-Leu-Leu-Asp-Ile-Ala-NH₂ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and β-END-LI and causes a very significant lowering of blood pressure.

EXAMPLE X

The peptide [D-Phe$^{12}$, Nle$^{21,38}$, Leu$^{36}$]-rCRF having the formula: H-Ser-Glu-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-His-Ser-Asn-Arg-Leu-Leu-Nle-Glu-Ile-Ile-NH$_2$ is synthesized. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and β-END-LI and causes a very significant lowering of blood pressure.

EXAMPLE XI

The peptide [D-Ala$^{24}$]-oCRF having the formula: H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-D-Ala-Asp-Gln-Leu-Ala-Gln-Gln-Ala-His-Ser-Asn-Arg-Lys-Leu-Asp-Ile-Ala-NH$_2$ is synthesized using a procedure generally as set forth in Example I.

Specific optical rotation of the oCRF peptide, which is synthesized and purified in the foregoing manner, is measured on a Perkin Elmer Model 241 Polarimeter as $[\alpha]_D^{22} = -79.4 \pm 1.0$ (c=0.5 in 1% acetic acid) (with correction for the presence of H$_2$O and TFA); it has a purity of about 98.9%.

The peptide is judged to be homogeneous using thin layer chromatography and several different solvent systems. It is specifically subjected to reversed-phase high pressure liquid chromatography using the Waters HPLC system described above with a 0.46×25 cm. column packed with 5 μm C$_{18}$ silica, 300 Å pore size. Buffer A which is used is an aqueous 0.1% trifluoroacetic acid solution consisting of 1.0 ml. of TFA per 1000 ml. of solution; Buffer B is 100% acetonitrile. The determination is run at room temperature with a gradient from 15.5% Buffer B to 71.5% Buffer B over 30 minutes. The flow rate is 1.8 ml. per minute, and the retention time is 21.9 minutes.

Amino acid analysis of the resultant, purified peptide is consistent with the formula for the prepared peptide and confirms that the 41-residue peptide structure is obtained.

EXAMPLE XII

The peptide [pGlu$^2$, D-Phe$^{12}$, D-Ala$^{24}$]-rCRF(2-41) having the formula: H-pGlu-Glu-Pro-Pro-Ile-Ser-Leu-Asp-:-Thr-D-Phe-His-Leu-Leu-Arg-Glu-Val-Leu-Glu-Met-Ala-Arg-D-Ala-Glu-Gln-Leu-Ala-Gln-Gln-Ala-His-Ser-Asn-Arg-Lys-Leu-Met-Glu-Ile-Ile-NH$_2$ is synthesized. Amino acid analysis of the resultant, purified peptide is consistent with the formula for the prepared peptide and confirms that the 40-residue peptide structure is obtained. Testing in accordance with the general procedure set forth hereinbefore shows that it likewise stimulates the secretion of ACTH and β-END-LI and causes a very significant lowering of blood pressure.

EXAMPLE XIII

The peptide [D-Glu$^{20}$, D-Ala$^{24}$, Nle$^{21,38}$]-oCRF having the formula: H-Ser-Gln-Glu-Pro-Pro-Ile-Ser-Leu-Asp-Leu-Thr-Phe-His-Leu-Leu-Arg-Glu-Val-Leu-D-Glu-Nle-Thr-Lys-D-Ala-Asp-Gln-Leu-Ala-Gln-Gln-Ala-His-Ser-Asn-Arg-Lys-Leu-Nle-Asp-Ile-Ala-NH$_2$ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and β-END-LI and causes a very significant lowering of blood pressure.

EXAMPLE XIV

The peptide [Benzoyl-Ser$^7$, D-Phe$^{12}$, Nle$^{21,38}$, D-His$^{32}$]-rCRF(7-41) having the formula: Bz-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-D-His-Ser-Asn-Arg-Lys-Leu-Nle-Glu-Ile-Ile-NH$_2$ is synthesized. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and β-END-LI and causes a very significant lowering of blood pressure.

EXAMPLE XV

The peptide [D-His$^{32}$]-oCRF having the formula: H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-D-His-Ser-Asn-Arg-Lys-Leu-Leu-Asp-Ile-Ala-NH$_2$ is synthesized using a procedure generally as set forth in Example I.

Specific optical rotation of the oCRF peptide, which is synthesized and purified in the foregoing manner, is measured on a Perkin Elmer Model 241 Polarimeter as $[\alpha]_D^{22} = -71.6 \pm 1.0$ (c=0.5 in 1% acetic acid) (with correction for the presence of H$_2$O and TFA); it has a purity of about 95.0%.

The peptide is judged to be homogeneous using thin layer chromatography and several different solvent systems. It is specifically subjected to reversed-phase high pressure liquid chromatography using the Waters HPLC system with a 0.46×25 cm. column packed with 5 μm C$_{18}$ silica, 300 Å pore size. Buffer A which is used is an aqueous 0.1% trifluoroacetic acid solution consisting of 1.0 ml. of TFA per 1000 ml. of solution; Buffer B is 100% acetonitrile. The determination is run at room temperature with a gradient from 36% Buffer B to 49% Buffer B over 20 minutes. The flow rate is 1.8 ml. per minute, and the retention time is 17.2 minutes.

Amino acid analysis of the resultant, purified peptide is consistent with the formula for the prepared peptide and confirms that the 41-residue peptide structure is obtained.

EXAMPLE XVI

The peptide [D-Phe$^{12}$, D-Glu$^{20}$, D-Ala$^{24}$, D-His$^{32}$]-rCRF(6-41) having the formula: H-Ile-Ser-Leu-Asp-Leu-Thr-D-Phe-His-Leu-Leu-Arg-Glu-Val-Leu-D-Glu-Met-Ala-Arg-D-Ala-Glu-Gln-Leu-Ala-Gln-Gln-Ala-D-His-Ser-Asn-Arg-Lys-Leu-Met-Glu-Ile-Ile-NH$_2$ is synthesized. Amino acid analysis of the resultant, purified peptide is consistent with the formula for the prepared peptide and confirms that the 36-residue peptide structure is obtained. Testing in accordance with the general procedure set forth hereinbefore shows that it likewise stimulates the secretion of ACTH and β-

END-LI and causes a very significant lowering of blood pressure.

EXAMPLE XVII

The peptide [D-Glu$^{20}$, Nle$^{21}$, D-His$^{32}$]-oCRF having the formula: H-Ser-Gln-Glu-Pro-Pro-Ile-Ser-Leu-Asp-Leu-Thr-Phe-His-Leu-Leu-Arg-Glu-Val-Leu-D-Glu-Nle-Thr-Lys-Ala-Asp-Gln-Leu-Ala-Gln-Gln-Ala-D-His-Ser-Asn-Arg-Lys-Leu-Leu-Asp-Ile-Ala-NH$_2$ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and β-END-LI and causes a very significant lowering of blood pressure.

EXAMPLE XVIII

The peptide [Acrylyl-Glu$^2$, D-Phe$^{12}$, Nle$^{21,38}$, D-His$^{32}$]-rCRF(2–41) having the formula: Acr-Glu-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln- Gln-Ala-D-His-Ser-Asn-Arg-Lys-Leu-Nle-Glu-Ile-Ile-NH$_2$ is synthesized. Amino acid analysis of the resultant, purified peptide is consistent with the formula for the prepared peptide and confirms that the 40-residue peptide structure is obtained. Testing in accordance with the general procedure set forth hereinbefore shows that it likewise stimulates the secretion of ACTH and β-END-LI and causes a very significant lowering of blood pressure.

EXAMPLE XIX

The peptide [D-phe$^{11}$, D-Glu$^{19}$, Ala$^{20}$, Arg$^{21}$, Glu$^{28}$, Ile$^{39}$]-sauvagine having the formula: pGlu-Gly-Pro-Pro-Ile-Ser-Ile-Asp-Leu-Ser-D-Phe-Glu-Leu-Leu-Arg-Lys-Met-Ile-D-Glu-Ala-Arg-Lys-Gln-Glu-Lys-Glu-Lys-Glu-Gln-Ala-Ala-Asn-Asn-Arg-Leu-Leu-Leu-Asp-Ile-Ile-NH$_2$ is synthesized. Testing in accordance with the general procedure set forth hereinbefore shows that it likewise stimulates the secretion of ACTH and β-END-LI and causes a very significant lowering of blood pressure.

EXAMPLE XX

The peptide [Nle$^{18,21}$, D-Glu$^{20}$, D-His$^{32}$]-AHC having the formula: H-Ser-Gln-Glu-Pro-Pro-Ile-Ser-Leu-Asp-Leu-Thr-Phe-His-Leu-Leu-Arg-Glu-Nle-Leu-D-Glu-Nle-Ala-Lys-Ala-Glu-Gln-Glu-Ala-Glu-Gln-Ala-D-His-Leu-Asn-Arg-Leu-Leu-Leu-Glu-Glu-Ala-NH$_2$ is synthesized. Testing in accordance with the general procedure set forth hereinbefore shows that it likewise stimulates the secretion of ACTH and β-END-LI and causes a very significant lowering of blood pressure.

EXAMPLE XXI

The peptide [D-Pro$^4$, D-Phe$^{12}$, Nle$^{21,38}$, CML$^{37}$-rCRF(4–41) having the formula: H-D-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-His-Ser-Asn-Arg-Lys-CML-Nle-Ile-Ile-NH$_2$ is synthesized. Specific optical rotation of the rCRF peptide is measured on a Perkin Elm Model 241 Polarimeter as $[\alpha]_D^{22} = -32.9 \pm 1.0$ (c=1 in 1% acetic acid)(with correction for the presence of H$_2$O and TFA); it has a purity of greater than 98%. Testing in accordance with the general procedure set forth hereinbefore shows that it likewise stimulates the secretion of ACTH and β-END-LI and causes a very significant lowering of blood pressure when injected peripherally.

EXAMPLE XXII

The peptide [D-Tyr$^3$, Nle$^{18}$, Nva$^{21}$, D-Glu$^{20}$, D-Ala$^{24}$]-AHC having the formula: H-Ser-Gln-D-Tyr-Pro-Pro-Ile-Ser-Leu-Asp-Leu-Thr-Phe-His-Leu-Leu-Arg-Glu-Nle-Leu-D-Glu-Nva-Ala-Lys-D-Ala-Glu-Gln-Glu-Ala-Glu-Gln-Ala-Ala-Leu-Asn-Arg-Leu-Leu-Leu-Glu-Glu-Ala-NH$_2$ is synthesized. Testing in accordance with the general procedure set forth hereinbefore shows that it likewise stimulates the secretion of ACTH and β-END-LI and causes a very significant lowering of blood pressure.

EXAMPLE XXIII

The peptide [Glu$^{2,13,22}$, D-Phe$^{12}$, Nle$^{18}$, Orn$^{23}$]-AHC having the formula: H-Ser-Glu-Glu-Pro-Pro-Ile-Ser-Leu-Asp-Leu-Thr-D-Phe-Glu-Lue-Leu-Arg-Glu-Nle-Leu-Glu-Met-Glu-Orn-Ala-Glu-Lys-Glu-Ala-Glu-Gln-Ala-Ala-Leu-Asn-Arg-Leu-Leu-Leu-Glu-Glu-Ala-NH$_2$. Testing in accordance with the general procedure set forth hereinbefore shows that it likewise stimulates the secretion of ACTH and β-END-LI and causes a very significant lowering of blood pressure.

EXAMPLE XXIV

The synthetic peptide [D-Phe$^{12}$, Glu$^{13}$, Ile$^{21}$, Lys$^{36}$, Tyr$^{37}$, Val$^{41}$]-AHC having the formula: H-Ser-Gln-Glu-Pro-Pro-Ile-Ser-Leu-Asp-Leu-Thr-D-Phe-Glu-Leu-Leu-Arg-Glu-Met-T-Glu-Ile-Ala-Lys-Ala-Glu-Gln-Glu-Ala-Glu-Gln-Ala-Ala-Leu-Asn-Arg-Lys-Tyr-Leu-Glu-Glu-Val-NH$_2$ is synthesized. Testing in accordance with the general procedure set forth hereinbefore shows that it likewise stimulates the secretion of ACTH and β-END-LI and causes a very significant lowering of blood pressure.

EXAMPLE XXV

The synthetic peptide [D-Phe$^{12}$, D-Glu$^{20}$, Arg$^{21}$]-AHC having the formula: H-Ser-Gln-Glu-Pro-Pro-Ile-Ser-Leu-Asp-Leu-Thr-D-Phe-His-Leu-Leu-Arg-Glu-Met-Leu-D-Glu-Arg-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized using a procedure generally as set forth in Example I. Testing in accordance with the general procedure set forth hereinbefore shows that it likewise stimulates the secretion of ACTH and β-END-LI and causes a very significant lowering of blood pressure.

EXAMPLE XXVI

The peptide [D-Phe$^{12}$, Nle$^{18,21}$, D-Ala$^{24}$]-AHC having the formula: H-Ser-Gln-Glu-Pro-Pro-Ile-Ser-Leu-Asp-Leu-Thr-D-Phe-His-Leu-Leu-Arg-Glu-Nle-Leu-Glu-Nle-Ala-Lys-D-Ala-Glu-Gln-Glu-Ala-Glu-Gln-Ala-Ala-Leu-Asn-Arg-Leu-Leu-Leu-Glu-Glu-Ala-NH$_2$ is synthesized. Testing in accordance with the general procedure set forth hereinbefore shows that it likewise stimulates the secretion of ACTH and β-END-LI and causes a very significant lowering of blood pressure.

EXAMPLE XXVII

The peptide [D-Glu$^{20}$, Nle$^{21,}$ CML$^{37}$]-oCRF having the formula: H-Ser-Gln-Glu-Pro-Pro-Ile-Ser-Leu-Asp- Leu-Thr-Phe-His-Leu-Leu-Arg-Glu-Val-Leu-D-Glu-Nle-Thr-Lys-Ala-Asp-Gln-Leu-Ala-Gln-Gln-Ala-His-Ser-Asn-Arg-Lys-CML-Leu-Asp-Ile-Ala-NH$_2$ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and $\beta$-END-LI and causes a very significant lowering of blood pressure.

EXAMPLE XXVIII

The peptide [D-Phe$^{12}$, Nle$^{21,38}$, CML$^{37}$]-oCRF having the formula: H-Ser-Gln-Glu-Pro-Pro-Ile-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Gln-Ala-His-Ser-Asn-Arg-Lys-CML-Nle-Asp-Ile-Ala-NH$_2$ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and $\beta$-END-LI and causes a very significant lowering of blood pressure.

EXAMPLE XXIX

The peptide [D-Glu$^{20}$, Nle$^{21,38}$, D-His$^{32}$, CML$^{37}$]-oCRF having the formula: H-Ser-Gln-Glu-Pro-Pro-Ile-Ser-Leu-Asp-Leu-Thr-Phe-His-Leu-Leu-Arg-Glu-Val-Leu-D-Glu-Nle-Thr-Lys-Ala-Asp-Gln-Leu-Ala-Gln-Gln-Ala-D-His-Ser-Asn-Arg-Lys-CML-Nle-Asp-Ile-Ala-NH$_2$ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and $\beta$-END-LI and causes a very significant lowering of blood pressure.

EXAMPLE XXX

The peptide [Formyl-Ser$^1$, D-Phe$^{12}$, Nle$^{21,38}$, D-His$^{32}$]-rCRF having the formula: For-Ser-Glu-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-D-His-Ser-Asn-Arg-Lys-Leu-Nle-Glu-Ile-Ile-NH$_2$ is synthesized. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and $\beta$-END-LI and causes a very significant lowering of blood pressure.

EXAMPLE XXXI

The peptide [D-Pro$^4$, D-Phe$^{12}$, Nle$^{18,21,38}$, CML$^{37}$]-rCRF(4–41) having the formula: H-D-Pro-Pro-Ile-Ser-Leu-Asp-Leu-Thr-D-Phe-His-Leu-Leu-Arg-Glu-Nle-Leu-Glu-Nle-Ala-Arg-Ala-Glu-Gln-Leu-Ala-Gln-Gln-Ala-His-Ser-Asn-Arg-Lys-CML-Nle-Glu-Ile-Ile-NH$_2$ is synthesized. Testing in accordance with the general procedure set forth hereinbefore shows that it likewise stimulates the secretion of ACTH and $\beta$-END-LI and causes a very significant lowering of blood pressure.

EXAMPLE XXXII

The peptide [D-Phe$^{12}$, Nle$^{21}$, Leu$^{38}$]-rCRF(3-41) having the formula: H-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-His-Ser-Asn-Arg-Lys-Leu-Tu-Glu-Ile-Ile-NH$_2$ is synthesized. Amino acid analysis of the resultant, purified peptide is consistent with the formula for the prepared peptide and confirms that the 39-residue peptide structure is obtained. Testing in accordance with the general procedure set forth in Example III shows that it likewise stimulates the secretion of ACTH and $\beta$-END-LI and causes a very significant lowering of blood pressure when administered peripherally.

EXAMPLE XXXIII

The peptide [D-Phe$^{12}$, Nle$^{21,38}$, Leu$^{36}$]-rCRF having the formula: H-Ser-Glu-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-His-Ser-Asn-Arg-Leu-Leu-Nle-Glu-Ile-Ile-NH$_2$ is synthesized. Amino acid analysis of the resultant, purified peptide is consistent with the formula for the prepared peptide and confirms that the 39-residue peptide structure is obtained. Testing in accordance with the general procedure set forth in Example III shows that it likewise stimulates the secretion of ACTH and $\beta$-END-LI and causes a very significant lowering of blood pressure when administered peripherally.

EXAMPLE XXXIV

The peptide [D-phe$^{12}$, Nle$^{21}$, Leu$^{36}$]-oCRF having the formula: H-Ser-Gln-Glu-Pro-Pro-Ile-Ser-Leu-Asp-Leu-Thr-D-Phe-His-Leu-Leu-Arg-Glu-Val-Leu-Glu-Nle-Thr-Lys-Ala-Asp- Gln-Leu-Ala-Gln-Gln-Ala-His-Ser-Asn-Arg-Leu-Leu-Leu-Asp-Ile-Ala-NH$_2$ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and $\beta$-END-LI and causes a very significant lowering of blood pressure.

EXAMPLE XXXV

The peptide [D-Phe$^{12}$, Nle$^{21,38}$]-oCRF having the formula: H-Ser-Gln-Glu-Pro-Pro-Ile-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Gln-Ala-His-Ser-Asn-Arg-Lys-Leu-Nle-Asp-Ile-Ala-NH$_2$ is synthesized using a procedure generally as set forth in Example I. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and $\beta$-END-LI and causes a very significant lowering of blood pressure.

CRF profoundly stimulates the pituitary-adrenalcortical axis, and CRF analogs should be useful to stimulate the functions of this axis in some types of patients with low endogenous glucocorticoid production. For example, CRF should be useful in restoring pituitary-adrenal function in patients having received exogenous glucocorticoid therapy whose pituitary-adrenalcortical functions remain suppressed.

Most other regulatory peptides have been found to have effects upon the central nervous system and upon the gastrointestinal tract. Because ACTH and β-END secretion is the "sine qua non" of mammal's response to stress, it was not surprising that CRF has significant effects on the brain as a mediator of the body's stress response. For example, CRF in the brain appears to increase respiratory rate and may be useful in treating respiratory depression. CRF may also find application in modifying the mood, learning and behavior of normal and mentally disordered individuals. Because CRF analogs elevate the levels of ACTH, β-END, β-lipotropin, other pro-opiomelano-cortin gene products and corticosterone, its administration can be used to induce their effects on the brain and periphery to thereby influence memory, mood, pain appreciation, etc., and more specifically, alertness, depression and/or anxiety. For example, when administered into the ventricles, CRF increases activity and improves learning performance in rats and thus may function as a natural stimulant.

CRF analogs should also be of use for increasing blood flow to the gastrointestinal tract of mammals, particularly humans and other mammals. All CRF related peptides have been shown to dilate the mesenteric vascular bed. Also, oCRF inhibits gastric acid production, and CRF analogs are expected to also be effective in the treatment of gastric ulcers by reducing gastric acid production and/o inhibiting gastrointestinal functions in a mammal.

CRF analogs or the nontoxic addition salts thereof, combined with a pharmaceutically or veterinarily acceptable carrier to form a pharmaceutical composition, may be administered to mammals, including humans, either intravenously, subcutaneously, intramuscularly, percutaneously, e.g. intranasally, intracerebrospinally or orally. The peptides should be at least about 90% pure and preferably should have a purity of at least about 98%; however, lower purities are effective and may well be used with mammals other than humans. This purity means that the intended peptide constitutes the stated weight percent of all like peptides and peptide fragments present. Administration to humans may be employed by a physician to lower blood pressure or to stimulate endogenous gluco-corticoid production. The required dosage will vary with the particular condition being treated, with the severity of the condition and with the duration of desired treatment.

These peptides may also be used to evaluate hypothalamic pituitary adrenal function in mammals with suspected endocrine or central nervous system pathology by suitable administration followed by monitoring body functions. For example, administration may be used as a diagnostic tool to evaluate Cushing's disease and affective disorders, such as depressive illness.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 1 to about 200 micrograms of the peptide per kilogram of the body weight of the host animal. In some instances, treatment of subjects with these peptides can be carried out in lieu of the administration of ACTH or corticosteroids, in such instances a dosage as low as about 10 ng/Kg of body weight may be employed. As used herein, all temperatures are ° C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the analogs. It appears important that the amino acid sequence from about positions 7 through 41 or equivalents thereof be present in the synthetic peptide, whereas the remainder of the molecule does not appear as critical. For instance, instead of the simple amide at the C-terminus, a lower alkyl-substituted amide, e.g. methylamide, ethylamide, etc, may be incorporated. Likewise from one to ten additional amino acid residues can be included at the N-terminus without significantly adversely affecting biological potency. Such peptides are considered as equivalents which fall within the scope of the invention.

Various features of the invention are emphasized in the claims which follow.

What is claimed is:

1. The CRF agonist peptide which is the CRF analog [D-Pro$^4$, D-Phe$^{12}$, Nle$^{21,38}$, CML$^{37}$]-rat CRF, having the formula: H-D-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-His-Ser-Asn-Arg-Lys-CML-Nle-Ile-Ile-NH$_2$, or a nontoxic salt thereof.

2. The CRF agonist peptide which is an analog of ovine CRF having the formula: H-Ser-Gln-Glu-Pro-Pro-Ile-Ser-:-Asp-Leu-Thr-D-Phe-His-Leu-Leu-Arg-Glu-Val-Leu-Glu-Nle-Thr-Lys-Ala-Asp-Gln-Leu-Ala-Gln-Gln-Ala-His-Ser-Asn-Arg-Lys-Leu-Leu-Asp-Ile-Ala-NH$_2$ or a nontoxic addition salt thereof.

3. A composition for stimulating secretion of ACTH and β-END-LI in mammals comprising an effective amount of a CRF agonist peptide or a nontoxic addition salt thereof in accordance with claim 2 and a pharmaceutically or veterinarily acceptable liquid or solid carrier therefor.

4. A CRF agonist peptide which is an analog of rat CRF having the following formula: H-Ser-Glu-Glu-Pro-Pro-Ile-Ser-Leu-Asp-Leu-Thr-D-Phe-His-Leu- Leu-Arg-Glu-Val-Leu-Glu-$R_{21}$-Ala-Arg-Ala-Glu-Gln-Leu-Ala-Gln-Gln-Ala-His-Ser-Asn-Arg-$R_{36}$-Leu-$R_{38}$-Glu-Ile-Ile-$NH_2$, wherein $R_{21}$ is Met or Nle; $R_{36}$ is Leu or Lys; and $R_{38}$ is Met, Leu or Nle; or having either of the above formulae wherein the N-terminus is shortened by one or a sequence of up to three residues, or a nontoxic addition salt thereof.

5. A CRF agonist peptide according to claim 4 wherein $R_{36}$ is Lys.

6. A CRF agonist peptide according to claim 4 wherein $R_{38}$ is Leu.

7. A CRF agonist peptide according to claim 5 wherein $R_{38}$ is Nle.

8. A CRF agonist peptide according to claim 5 wherein $R_{21}$ is Nle.

9. A CRF agonist peptide according to claim 6 wherein $R_{21}$ is Nle.

10. A CRF agonist peptide according to claim 7 wherein $R_{21}$ is Nle.

11. A CRF agonist peptide according to claim 4 which is [D-Phe$^{12}$, Nle$^{21,38}$, Leu$^{36}$]-rat CRF.

* * * * *

UNITED STATES PATENT AND TRADEMARK OFFICE
CERTIFICATE OF CORRECTION

PATENT NO. : 5,278,146
DATED : January 11, 1994
INVENTOR(S) : Rivier, et al

It is certified that error appears in the above-indentified patent and that said Letters Patent is hereby corrected as shown below:

Column 18 (claim 2), lines 56 and 57 should read: --Pro-Ile-Ser-Leu-Asp-Leu-Thr-D-Phe-His-Leu-Leu-Arg-Glu-Val-Leu-Glu-Met-Thr-Lys-Ala-Asp-Gln-Leu-Ala--; Column 19, (claim 4), line 3, before "wherein", insert the following: --or which is an analog of ovine CRF having the following formula:
H-Ser-Gln-Glu-Pro-Pro-Ile-Ser-Leu-Asp-Leu-Thr-D-Phe-His-Leu-Leu-Arg-Glu-Val-Leu-Glu-$R_{21}$-Thr-Lys-Ala-Asp-Gln-Leu-Ala-Gln-Gln-Ala-His-Ser-Asn-Arg-$R_{36}$-Leu-$R_{38}$-Asp-Ile-Ala-$NH_2$,--.

Signed and Sealed this

Twenty-eighth Day of November 1995

Attest:

BRUCE LEHMAN

*Attesting Officer*       *Commissioner of Patents and Trademarks*